(12) United States Patent
Maruyama et al.

(10) Patent No.: US 9,068,021 B2
(45) Date of Patent: *Jun. 30, 2015

(54) LOW-SUBSTITUTED HYDROXYPROPYLCELLULOSE POWDER

(71) Applicant: Shin-Etsu Chemical Co., Ltd., Tokyo (JP)

(72) Inventors: Naosuke Maruyama, Joetsu (JP); Hiroshi Umezawa, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,773

(22) Filed: Jul. 29, 2013

(65) Prior Publication Data

US 2013/0316176 A1 Nov. 28, 2013

Related U.S. Application Data

(62) Division of application No. 11/888,375, filed on Aug. 1, 2007, now Pat. No. 8,519,120.

(30) Foreign Application Priority Data

Aug. 8, 2006 (JP) .................... 2006-215401
Oct. 23, 2006 (JP) .................... 2006-287858

(51) Int. Cl.
*C08B 11/08* (2006.01)
*A61K 9/20* (2006.01)

(52) U.S. Cl.
CPC ............ *C08B 11/08* (2013.01); *Y10T 428/2982* (2015.01); *A61K 9/2054* (2013.01)

(58) Field of Classification Search
CPC ....... C08B 11/08; A61K 47/38; A61K 9/2054
See application file for complete search history.

(56) References Cited

U.S. PATENT DOCUMENTS

| | | | |
|---|---|---|---|
| 3,351,583 A | 11/1967 | Bishop | |
| 3,852,421 A | 12/1974 | Koyanagi et al. | |
| 4,091,205 A | 5/1978 | Onda et al. | |
| 4,292,426 A | 9/1981 | Orii et al. | |
| 4,491,661 A | 1/1985 | Bredereck et al. | |
| 5,028,433 A | 7/1991 | Ishimaru et al. | |
| 6,525,192 B2 | 2/2003 | Obara et al. | |
| 6,602,995 B2 | 8/2003 | Maruyama et al. | |
| 6,884,883 B1 | 4/2005 | Shima et al. | |
| 2002/0016452 A1 | 2/2002 | Obara et al. | |
| 2003/0125543 A1 | 7/2003 | Obara et al. | |
| 2003/0224043 A1 | 12/2003 | Appel et al. | |
| 2004/0167224 A1 | 8/2004 | Ozaki et al. | |
| 2006/0204572 A1 | 9/2006 | Higuchi et al. | |

FOREIGN PATENT DOCUMENTS

| | | |
|---|---|---|
| EP | 0497331 A2 | 8/1992 |
| EP | 0662320 A1 | 7/1995 |
| EP | 1054019 A1 | 11/2000 |
| EP | 1099709 A1 | 5/2001 |
| EP | 1319670 A1 | 6/2003 |
| EP | 0957112 B1 | 9/2003 |
| EP | 1514547 A1 | 3/2005 |
| EP | 1854463 A1 | 11/2007 |
| EP | 1967211 A1 | 9/2008 |
| GB | 1479557 | 7/1977 |
| JP | 48-38858 | 11/1973 |
| JP | 57-53100 | 11/1982 |
| JP | 7-324101 | 12/1995 |
| JP | 9-76233 | 3/1997 |
| JP | 10-305084 | 11/1998 |
| JP | 11-322802 | 11/1999 |
| JP | 2001-9316 | 1/2001 |
| JP | 2004-067606 A | 3/2004 |
| JP | 2005-517690 A | 6/2005 |
| WO | WO 97/46224 A1 | 12/1997 |
| WO | WO 00/57881 A1 | 10/2000 |
| WO | WO 03/063831 A2 | 8/2003 |
| WO | WO 2004/058257 A1 | 7/2004 |
| WO | WO 2005/046696 A1 | 5/2005 |
| WO | WO 2007/108010 A2 | 9/2007 |

OTHER PUBLICATIONS

Alvarez-Lorenzo et al., Eur. J. Pharm. Biopharm., 2000, 50, p. 307-318.*
JPO machine translation of JP 07324101 A, http://dossier1.ipdl.inpit.go.jp/, accessed online on Dec. 12, 2013.*
Gustafsson et al., Eur. J. Pharm. Sci., 1999, 9, p. 171-184.*
Alvarez-Lorenzo et al. "Evaluation of low-substituted hydroxypropylcelluloses (L-HPCs) as filler-binders for direct compression" *International J. of Pharmaceutics* 197:107-116 (2000).
European search report corresponding to European Patent Application No. 07015394.5-1214 dated Mar. 5, 2008.
Chinese Office Action corresponding to Chinese Patent Application No. 200710140179.0 mailed Jul. 23, 2009.
R. J. Harwood "Hydroxypropyl Cellulose, Low-substituted", *Handbook of Pharmaceutical Excipients*, 5th Ed., Pharmaceutical Press pp. 341-343 (2006).
European Search Report corresponding to European Patent Application No. 07015395.2 mailed Oct. 2, 2009.
European Search Report corresponding to European Patent Application No. 07015396.0 mailed Oct. 2, 2009.
Rowe et al, "Hydroxypropyl Cellulose, Low-substituted", *Handbook of Pharmaceutical Excipients*, 5th Ed., Pharmaceutical Press pp. 341-343 (2006).
Examination Report corresponding to Indian Patent Application No. 1734/CHE/2007 dated Mar. 10, 2011.
Examination Report corresponding to Indian Patent Application No. 1736/CHE/2007 dated Mar. 10, 2011.
Japanese Office Action corresponding to Japanese Application No. 2007-206387 mailed Jun. 1, 2012.
Japanese Office Action corresponding to Japanese Application No. 2007-206388 mailed Apr. 13, 2012.
Japanese Office Action corresponding to Japanese Application No. 2007-206389 mailed Mar. 27, 2012.

* cited by examiner

*Primary Examiner* — Jonathan S Lau
(74) *Attorney, Agent, or Firm* — Myers Bigel Sibley & Sajovec, P.A.

(57) ABSTRACT

Provided is a low-substituted hydroxypropylcellulose powder having high compressibility, good flowability and excellent disintegration. The powder has an average particle size of 10 to 100 μm and a specific surface area measured by BET method of at least 1.0 $m^2/g$.

3 Claims, 2 Drawing Sheets

LOW-SUBSTITUTED HYDROXYPROPYLCELLULOSE POWDER

CROSS-REFERENCE TO RELATED APPLICATION

This application is a divisional of U.S. patent application Ser. No. 11/888,375, now allowed, filed Aug. 1, 2007, which claims priority to Japanese Patent Application No. 2006-215401, filed Aug. 8, 2006 and Japanese Patent Application No. 2006-287858, filed Oct. 23, 2006, the disclosures of which are incorporated herein by reference in their entirety.

FIELD AND BACKGROUND OF THE INVENTION

The present invention relates to low-substituted hydroxypropylcellulose that is added for providing disintegration or compressibility at the time of production of a preparation, in the field of medicines, foods, or the like. More specifically, the present invention relates to low-substituted hydroxypropylcellulose that is excellent in particular in compressibility and disintegration.

In solid dosage forms in the field of medicines, foods, or the like, a preparation produced only from a principal ingredient has the problems that the drug action may not be sufficiently exerted because sufficient disintegration is not obtained when the drug is administered, and that the shape of a tablet or a granule produced therefrom may not be kept due to its poor compressibility. In this case, the disintegration can be improved by adding a disintegrant such as low-substituted hydroxypropylcellulose, calcium salts of carboxymethyl cellulose, crosslinked carboxymethylcellulose sodium, crosslinked polyvinylpyrrolidone, or carboxymethyl starch. Furthermore, the compressibility can be improved by adding crystalline cellulose or a water-soluble binder. Low-substituted hydroxypropylcellulose is known as a unique additive having both of the disintegration and the compressibility.

Since low-substituted hydroxypropylcellulose is nonionic, there is an advantage in that alteration is less caused by reaction with an ionic drug, for example. Japanese Patent Application Examined Publication Nos. 48-38858/1973 and 57-53100/1982 described that low-substituted hydroxypropylcellulose can be used as an additive of medicines.

As described in Japanese Patent Application Examined Publication No. 48-38858/1973, Japanese Patent Application Examined Publication No. 57-53100/1982, Japanese Patent Application Unexamined Publication No. 10-305084/1998, Japanese Patent Application Unexamined Publication No. 11-322802/1999, and Japanese Patent Application Unexamined Publication No. 7-324101/1995, examples of a method for preparing alkali cellulose include a method in which sheet-shaped pulp is immersed in an aqueous sodium hydroxide solution and then squeezed. In this method, sheet-shaped pulp is immersed in an aqueous sodium hydroxide solution, and thus an excessive amount of aqueous sodium hydroxide solution is absorbed by the pulp. Accordingly, when the pulp is squeezed, all that is produced is alkali cellulose containing an excessive amount of water or sodium hydroxide. Thus, the selectivity for side reactions increases, and the efficiency of etherification, which is a main reaction, is low.

As described in Japanese Patent Application Unexamined Publication No. 10-305084/1998, conventional low-substituted hydroxypropylcellulose can be obtained by reacting alkali cellulose and propylene oxide. In etherification, cellulose is etherified as a main reaction, and propylene glycol is produced as a side reaction due to reaction between propylene oxide and water. The amount of propylene oxide used for this etherification varies depending on the amount of aqueous sodium hydroxide solution used as a reaction catalyst, and there is the problem that the reaction efficiency is lowered when the amount of water or sodium hydroxide in the alkali cellulose is too large.

On the other hand, a production method in which an aqueous sodium hydroxide solution is dropped or sprayed and thus mixed with powdered pulp is advantageous in that the amount of water of sodium hydroxide in the alkali cellulose can be freely adjusted.

Furthermore, as described in Japanese Patent Application Unexamined Publication No. 10-305084/1998, in a case where a crude reaction product is dissolved by loading the reaction product into hot water containing acids during neutralization of alkali remaining in the crude reaction product, then obtained low-substituted hydroxypropylcellulose is in the form of fibers as in the raw material pulp, is excellent in washability, and can be easily refined, but it is poor in milling characteristics, and thus a powder having excellent flowability cannot be obtained.

Japanese Patent Application Examined Publication No. 57-53100/1982 described a method for controlling fiber portions by partially neutralizing alkali used as a reaction catalyst in water, and partially dissolving low-substituted hydroxypropylcellulose, after completion of etherification. It was described that in this method, when the amount of alkali remaining is increased, the amount of fibrous substances is reduced due to dissolution, so that an obtained milled product has high bulk density and good flowability, but the washability is lowered at the time of refinement.

Japanese Patent Application Unexamined Publication No. 10-305084/1998 described that when the water content of a washed and dehydrated product is 70 to 90% by weight, the milling characteristics are improved, and thus a low-substituted hydroxypropylcellulose powder can be obtained that has a degree of compression of 42% or less and a repose angle of 48° or less. It was also described that milling is performed using an impact-type mill such as a hammer mill.

However, in an impact-type mill, a product is easily affected by the influence of a milling raw material, and the powder properties of the product are determined by the shape of the milling raw material. More specifically, when milling, with an impact-type mill, fibrous raw materials that are obtained by increasing the partial neutralization amount as in Japanese Patent Application Unexamined Publication No. 57-53100/1982, or by performing neutralization by loading a reaction product into water or hot water containing acids in an amount equivalent to sodium hydroxide that remains in the crude reaction product, without performing a dissolution step, then the obtained milled product is a powder containing a large amount of fibrous particles and having low flowability. Furthermore, this method has low throughput and low productivity because milling is performed by applying high energy in a short time.

Furthermore, low-substituted hydroxypropylcellulose produced by the above-described method has a problem in that when dissolution is performed with a smaller partial neutralization amount in order to improve the flowability of a powder, the amount of fiber portions is reduced and thus the compressibility is lowered. Furthermore, when the amount of fiber portions is increased by increasing the partial neutralization amount in order to improve the compressibility, there is a problem in that the flowability is lowered.

The powder obtained according to Japanese Patent Application Unexamined Publication No. 10-305084/1998, in which the water content of a washed and dehydrated product is controlled to 70 to 90% by weight, contains fibrous particles and spherical particles in a mixed manner. Due to the influence of the fibrous particles, the flowability is insufficient. Thus, when a tablet is produced by direct tableting, the weight variation of the tablet may be large. Furthermore, due to low compressibility of the spherical particles, the compressibility of the mixed powder is insufficient.

Japanese Patent Application Unexamined Publication No. 11-322802/1999 described that when fibrous particles are completely dissolved, low-substituted hydroxypropylcellulose having high flowability can be obtained. However, the compressibility of a powder obtained by this method is low.

Furthermore, Japanese Patent Application Examined Publication No. 57-53100/1982 described that when milling is performed using a ball mill instead of impact milling, the compressibility is poor. Moreover, when milling is performed using a ball mill, the swelling properties, which are important properties as a disintegrant, are low.

Japanese Patent Application Unexamined Publication No. 2001-9316 described water-soluble cellulose ether in which a vertical roller mill is used for powdering pulp, and thus the bulk density of the powdered pulp is increased, so that the amount of fibers that are not dissolved when the cellulose ether is dissolved in water is small.

However, water-soluble cellulose ether is different from water-insoluble low-substituted hydroxypropylcellulose, in that a neutralization step, which is essential for producing low-substituted hydroxypropylcellulose, is not performed. Furthermore, in Japanese Patent Application Unexamined Publication No. 2001-9316, there is no description on compressibility and disintegration, which are important properties of low-substituted hydroxypropylcellulose.

Japanese Patent Application Unexamined Publication No. 9-76233/1997 described a method for producing cellulose ether using a vertical roller mill, but this method relates not to water-insoluble low-substituted hydroxypropylcellulose but to water-soluble cellulose ether, in a similar manner.

Japanese Patent Application Unexamined Publication No. 7-324101/1995 described low-substituted hydroxypropylcellulose having a repose angle of 45° or less and a swollen volume increase ratio of 100% or more, but the compressibility of this low-substituted hydroxypropylcellulose is low.

SUMMARY OF THE INVENTION

The present invention was completed for solving the problems of the above-descried conventional techniques. It is an object thereof to provide a low-substituted hydroxypropylcellulose powder having high compressibility, good lowability and excellent disintegration, and a method for producing the same.

The inventors had conducted an in-depth study in order to achieve the above-described object, and found that a low-substituted hydroxypropylcellulose powder having high compressibility, good flowability and excellent disintegration can be obtained by the method for producing low-substituted hydroxypropylcellulose wherein an aqueous sodium hydroxide solution is added to and mixed with powdered pulp so as to produce alkali cellulose in which the weight ratio of sodium hydroxide with respect to anhydrous cellulose is 0.1 to 0.3; the alkali cellulose is etherified; subsequently, the sodium hydroxide is neutralized after performing or without performing a dissolution step; the resultant is washed and dried; and then the dried product is compaction-ground in a pulverization step.

More specifically, the present invention provides a method for producing a low-substituted hydroxypropylcellulose powder having a molar substitution number per anhydrous glucose unit (in other words, the number of moles substituted with hydroxypropoxyl groups per anhydrous glucose unit) of 0.05 to 1.0, which is insoluble in water and swollenable by absorbing water, comprising the steps of: (1) adding an aqueous sodium hydroxide solution to powdered pulp in such a manner that weight ratio of sodium hydroxide with respect to anhydrous cellulose is 0.1 to 0.3 so as to obtain alkali cellulose; (2) etherifying the obtained alkali cellulose so as to obtain a crude reaction product; (3) neutralizing the sodium hydroxide contained in the obtained crude reaction product; (4) washing and dehydrating the resultant; (5) drying; and (6) pulverizing by using compaction-grinding. Furthermore, the present invention provides a method for producing a low-substituted hydroxypropylcellulose powder having a molar substitution number per anhydrous glucose unit of 0.05 to 1.0, which is insoluble in water and swollenable by absorbing water, comprising the steps of: (1) adding an aqueous sodium hydroxide solution to powdered pulp in such a manner that the weight ratio of sodium hydroxide with respect to anhydrous cellulose is 0.1 to 0.3 so as to obtain alkali cellulose; (2) etherifying the obtained alkali cellulose so as to obtain a crude reaction product; (3) neutralizing the sodium hydroxide contained in the obtained crude reaction product without performing a step of dissolving part or whole of the crude reaction product; (4) washing and dehydrating the resultant; (5) drying; and (6) pulverizing using by compaction-grinding.

It is preferable that in said step of washing and dehydrating, said resultant is washed and dehydrated such that a water content is not greater than 65% by weight. Furthermore, the present invention provides a low-substituted hydroxypropylcellulose powder having an average particle size of 10 to 100 μm and a specific surface area measured by BET method of at least 1.0 $m^2/g$. It is preferable that the low-substituted hydroxypropylcellulose powder has an elastic recovery ratio of not greater than 7% when compressed at a compression force of 50 MPa. It is preferable that the low-substituted hydroxypropylcellulose powder has a swollen volume increase ratio of at least 300% and a swollen volume increase rate of at least 100%/min when absorbing water. It is preferable that the low-substituted hydroxypropylcellulose powder has a repose angle of not greater than 42°.

Moreover, the present invention provides a solid dosage form using this low-substituted hydroxypropylcellulose powder.

The low-substituted hydroxypropylcellulose powder of the present invention has high flowability, excellent compressibility and excellent swelling properties, regardless of the fibrous form derived from raw material pulp.

The low-substituted hydroxypropylcellulose powder of the present invention is advantageous also in that due to its excellent compressibility and excellent disintegration, the amount of this powder added to a tablet can be reduced, and thus the size of the tablet can be made smaller.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. Hereinafter, preferred embodiments of the present invention will be described. However, it is to be understood that the present invention is not limited thereto.

First, any milling method may be applied for obtaining powdered pulp that is used as a raw material. The average particle size thereof is preferably 60 to 300 μm. It may be inefficient from an industrial viewpoint to prepare powdered pulp having an average particle size of less than 60 μm. If the average particle size is more than 300 μm, then the uniformity with an aqueous sodium hydroxide solution may be poor.

The step of producing alkali cellulose is preferably performed by dropping or spraying the aqueous sodium hydroxide solution to the powdered pulp and mixing the resultant. At that time, the sodium hydroxide acts as a catalyst in the etherification. The alkali cellulose may be produced preferably by using either a method in which mixing is performed in an internally-agitating type reaction device, and then etherification is successively performed, or a method in which alkali cellulose prepared in another mixing device is charged into a reaction device, and etherification is performed.

Furthermore, it was found that the amount of the sodium hydroxide in the alkali cellulose affects not only the reaction efficiency but also the swelling properties and the compressibility of final products. The optimum amount of the sodium hydroxide in the alkali cellulose may be 0.1 to 0.3 in the weight ratio of the sodium hydroxide with respect to anhydrous cellulose (referring to the balance obtained by removing water from the pulp). If the amount is less than 0.1, then the swelling properties, in particular, the volume increase ratio when the product is swollen by absorbing water may be lowered, the disintegration may be lowered, and the compressibility also may be lowered. Furthermore, if the amount is more than 0.3, then the swollen volume increase ratio and the swollen volume increase rate when absorbing water (described later) may be lowered, and the compressibility also may be lowered.

The sodium hydroxide is preferably added as an aqueous 20 to 40% by weight solution.

The following etherification step may be performed by charging the alkali cellulose into a reaction device, performing nitrogen purge, and then charging propylene oxide into the reaction device as an etherifying agent, thereby causing a reaction. The charge of the propylene oxide charged is preferably approximately 0.1 to 1.0 mole with respect to 1 mole of anhydrous glucose units. The reaction temperature is approximately 40 to 80° C., and the reaction time is approximately 1 to 5 hours.

It should be noted that after the etherification step, a dissolution step may be performed, if necessary. The dissolution step is performed by dissolving part or whole of the crude reaction product after the etherification in water or hot water. The amount of water or hot water used varies depending on the amount of the crude reaction product to be dissolved, but the amount of water for dissolving whole of the crude reaction product is usually 0.5 to 10 in the weight ratio with respect to the low-substituted hydroxypropylcellulose in the crude reaction product.

In order to further improve the load in the wash and dehydration step described later, and the compressibility of low-substituted cellulose ether, it is preferable not to perform the dissolution step.

In the following neutralization step, since the sodium hydroxide used as the catalyst remains in the reaction product, neutralization is preferably performed by loading the crude reaction product into water or hot water containing acids in an amount equivalent to the sodium hydroxide. Alternatively, neutralization may be performed by adding water or hot water containing the equivalent amount of acids to the reaction product.

Examples of the acids that are used herein include mineral acids such as hydrochloric acid, sulfuric acid, and nitric acid, and organic acids such as fomic acid and acetic acid.

In the following wash and dehydration step, while washing the obtained neutralized product preferably using water or hot water, dehydration is performed by a method preferably selected from centrifugation, suction filtration, and pressure filtration, for example. The low-substituted hydroxypropylcellulose in an obtained dehydrated product cake is in the form of fibers as in the raw material pulp. The dehydrated product obtained after performing the dissolution step has a dehydration ratio of approximately 70 to 90% by weight, although this ratio depends on the number of moles substituted. The dehydration ratio of the dehydrated product obtained without performing the dissolution step is usually 65% by weight or less, so that the load in the following drying step can be reduced, and the productivity is improved. Furthermore, it is advantageous in that the steps can be simplified because the dissolution step is not included.

Furthermore, in view of the compressibility of the product, when milling a fibrous substance, the obtained product has higher specific surface area and thus higher compressibility.

The drying step of drying the obtained dehydrated product is preferably performed using a drier such as a fluidized bed drier or a drum drier at 60 to 120° C.

The milling step is performed by compaction-grinding the dried product obtained by the above-described method.

For this compaction-grinding, mills such as a roller mill, a ball mill, a bead mill, or a millstone mill can be used. In a roller mill, with a centrifugal force or gravity load accompanying its rotational movement, rollers or balls roll over while compressing/shearing a milling target on a mill wall. Examples thereof include an IS mill manufactured by Ishikawajima-Harima Heavy Industries Co., Ltd., a VX mill manufactured by Kurimoto, Ltd., and an MS roller mill manufactured by MASUNO SEISAKUSHO LTD. A ball mill uses, as a milling medium, steel balls, magnetic balls, cobbled stones, or the like. Examples thereof include a ball mill manufactured by KURIMOTO TEKKO KK, a tube mill manufactured by Otsuka Iron Works, and a planetary ball mill manufactured by FRITSCH. A bead mill is similar to the ball mill, but is different therefrom in that the diameter of balls used is smaller and in that acceleration of the balls can be further increased by rotating the internal portion of the device at high speed. Examples thereof include a bead mill manufactured by Ashizawa. A millstone mill can grind a powder by rotating a millstone at narrow clearance at high speed. Examples thereof include Serendipiter manufactured by MASUKO SANGYO CO., LTD.

The roller mill is particularly preferable because it reduces foreign metal substances mixed in, requires small installation area, and provides high productivity.

It has been considered that the compressibility of low-substituted hydroxypropylcellulose produced by conventional impact milling is exerted by intertwining of fibrous substances. When fibrous particles are increased based on this idea for improving the compressibility, the flowability is lowered. However, a low-substituted hydroxypropylcellulose powder of the present invention exhibits surprisingly high compressibility, although the fibrous form has been lost due to the compaction-grinding.

As described in Japanese Patent Application Examined Publication No. 57-53100/1982 and Japanese Patent Application Unexamined Publication No. 10-305084/1998, the powder properties of the product have been conventionally adjusted by controlling the amount of fibrous particles, by partially neutralizing sodium hydroxide used as a reaction catalyst in water, and partially dissolving low-substituted hydroxypropylcellulose, after completion of etherification. Furthermore, in Japanese Patent Application Unexamined Publication No. 11-322802/1999, a powder having high flowability is prepared by completely dissolving low-substituted hydroxypropylcellulose. In all of these methods, milling is performed using an impact-type mill such as an impact mill that uses an impact force.

In an impact-type mill, a product is easily affected by the influence of a milling raw material, and the powder properties of the product are determined by the shape of the milling raw material. More specifically, in a case where fibrous raw materials are used that are obtained, as in Japanese Patent Application Examined Publication No. 57-53100/1982 and Japanese Patent Application Unexamined Publication No. 10-305084/1998, by increasing the partial neutralization amount, or by performing neutralization by loading a reaction product into water or hot water containing acids in an amount equivalent to sodium hydroxide that remains in the crude reaction product, without performing a dissolution step that is an embodiment of the present invention, then the obtained pulverized product is a powder containing a large amount of fibrous particles and having low flowability.

According to the present invention, when fibrous particles serving as a milling raw material may be repeatedly compaction-ground, the fibrous and hollow tubular form derived from the raw material pulp is lost, and thus primary particles can be made smaller, so that the specific surface area is increased. Also, since the fibrous form derived from the raw material pulp is lost, a powder having uniform particle shape can be obtained.

Next, preferably, the pulverized product may be sieved following the usual method, and thus the targeted low-substituted hydroxypropylcellulose powder can be obtained. The opening of a sieve herein may be approximately 75 to 180 μm.

The average particle size of the low-substituted hydroxypropylcellulose powder of the present invention is preferably approximately 10 to 100 μm, and more preferably approximately 20 to 60 μm. If the average particle size is less than 10 μm, then aggregability increases because the hydroxypropylcellulose is in the form of fine powder, and thus the flowability of the powder may be lowered. If the average particle size is more than 100 μm, then uniformity with the drug is lowered, and thus the product may be non-uniform.

The specific surface area of the low-substituted hydroxypropylcellulose powder of the present invention is preferably 1.0 $m^2/g$ or more. If the specific surface area is less than 1.0 $m^2/g$, then high compressibility may not be obtained.

It is known that generally, higher specific surface area of a powder provides higher compressibility of the powder. The specific surface area analysis is a method for obtaining the specific surface area of a sample based on the amount of molecules adsorbed to the surface of particles of the powder at the temperature of liquid nitrogen, the molecules having adsorption occupying area that has been known. For the specific surface area analysis, the BET method can be used that is based on physical adsorption of inert gas at low temperature and low humidity. In the measurement, for example, MICROMERITICS GEMINI 2375 (manufactured by SHIMADZU CORPORATION) can be used.

Generally, specific surface area can be increased by reducing average particle size. However, as described above, if average particle size is too small, then the aggregability of a powder increases, and the flowability of the powder may be lowered. In the present invention, using compaction-grinding, a powder is provided that has high specific surface area although its average particle size is sufficient for securing the flowability of the powder.

Elastic recovery ratio refers to an indicator of the compressibility of a powder. The elastic recovery ratio can be calculated from the following equation, based on the thickness of a tablet obtained by compression a powder in a tablet weight of 480 mg and at a compression force of 50 MPa, using a flat shape with a flat contact face for a tablet diameter of 11.3 mm.

Elastic recovery ratio={(tablet thickness after 30 seconds−minimum tablet thickness)/(minimum tablet thickness)}×100

Herein, "minimum tablet thickness" refers to the lowest point obtained when the powder is compressed by an upper punch of a flat shape unit with a fixed lower punch, that is, the thickness obtained when the tablet is compressed to the extent possible. "Tablet thickness after 30 seconds" refers to the tablet thickness at 30 seconds after the upper punch is removed upward.

The elastic recovery ratio of the low-substituted hydroxypropylcellulose powder of the present invention is preferably 7% or less, and it was found that this low-substituted hydroxypropylcellulose powder is a plastically deformable member similar to crystalline cellulose commonly used as a binder, and is a powder that forms a dense molded product in a compressed state. A powder produced by the method described in Patent Japanese Patent Application Examined Publication No. 57-53100/1982 and Japanese Patent Application Unexamined Publication No. 2001-9316 has high elastic recovery ratio and substantially is an elastically deformable member.

The swelling properties of the low-substituted hydroxypropylcellulose powder of the present invention can be measured, for example, in the following manner: the low-substituted hydroxypropylcellulose powder is molded at a compression forge of 1 t into a tablet having a flat face with a diameter of 15 mm; the tablet is swollen by dropping water thereonto; and the swelling properties are evaluated as the swollen volume increase ratio and the swollen volume increase rate at that time. When alkali cellulose is used in which the weight ratio of sodium hydroxide with respect to anhydrous cellulose is 0.1 to 0.3, the swollen volume increase ratio is preferably 300% or more, and the swollen volume increase rate is preferably 100%/min or more.

The swollen volume increase ratio can be obtained in the following manner: the powder is molded at a compression force of 1 t into a tablet having a flat face with a diameter of 15 mm; a punch with a pipe is attached instead of the upper punch; the tablet is caused to absorb water for 10 minutes by dropping water through this pipe onto the tablet contained in a mortar; and the swollen volume increase ratio is obtained at that time. The water is dropped at a rate of 1 ml/min for 10 minutes. The increase in the volume can be calculated from the following equation, based on a change in the thickness of the tablet.

$$\text{Swollen volume increase ratio} = (\text{difference in tablet thickness between before and after adding water}/\text{tablet thickness before adding water}) \times 100$$

It should be noted that in the equation above, "difference in tablet thickness between before and after adding water" refers to a value obtained by subtracting the tablet thickness before adding water from the tablet thickness after adding water for 10 minutes.

The swollen volume increase ratio of the low-substituted hydroxypropylcellulose powder of the present invention is preferably 300% or more in view of swelling properties, which are important properties as the disintegrant. If the swollen volume increase ratio is less than 3000, then the disintegration time of a preparation produced from the powder may be longer.

The swollen volume increase rate refers to an initial swelling ratio at 30 seconds after starting the addition of water, when the swollen volume increase ratio is measured under the same condition as the above-described method, and can be calculated from the following equation.

$$\text{Swollen volume increase rate} = (\text{difference in tablet thickness before and after initially adding water}/\text{tablet thickness before adding water}) \times 100/0.5$$

In the equation above, "difference in tablet thickness before and after initially adding water" refers to a value obtained by subtracting the tablet thickness before adding water from the tablet thickness at 30 seconds after starting the addition of water.

The swollen volume increase rate of the low-substituted hydroxypropylcellulose powder of the present invention is preferably 100%/min or more in view of swelling properties, which are important properties as the disintegrant. If the swollen volume increase rate is less than 100%/min, then the disintegration time of a preparation produced from the powder may be longer.

The low-substituted hydroxypropylcellulose powder of the present invention is a powder having high flowability and preferably having a repose angle of 42° or less, the repose angle being one type of indicators of the flowability of a powder. The repose angle refers to an angle formed by a horizontal plane and a generatrix of a corn that is a deposition formed by dropping the sample onto the plane. For example, using a powder tester PT-D (manufactured by Hosokawa Micron Corporation), the repose angle can be calculated by allowing the sample to flow from a height of 75 mm onto a disc-shaped metal stage having a diameter of 80 mm, until a constant angle is obtained, and then measuring the angle formed by the deposited powder and the stage. The smaller this angle is, the better the flowability of the powder is.

Furthermore, as an indicator of compressibility, the hardness of a tablet can be evaluated when the tablet is obtained by compression a sample powder in a tablet weight of 480 mg and at a compression force of 150 MPa, using a flat shape for a tablet diameter of 11.3 mm. The hardness of a tablet obtained using the low-substituted hydroxypropylcellulose powder of the present invention is preferably 35 kgf or more, and particularly preferably 40 kgf or more. Tablet hardness can be evaluated, for example, by performing tableting under the above-described conditions using a tableting tester (manufactured by SANKYO PIO-TECH. CO., Ltd.). It should be noted that tableting is preferably performed at a constant water content of a sample powder, because the obtained tablet hardness varies depending on the water content of the sample powder. Tableting is preferably performed after adjusting the water content of the sample powder, for example, to 2 to 4% by weight.

Furthermore, evaluation can be performed also based on the bulk density of the low-substituted hydroxypropylcellulose powder. For example, bulk density can be obtained using a powder tester (manufactured by Hosokawa Micron Corporation), by measuring the weight when loosely filling (that is, without tapping) a vessel with a volume of 100 ml. The bulk density of the low-substituted hydroxypropylcellulose powder of the present invention is preferably 0.3 to 0.5 g/ml, and particularly preferably 0.35 to 0.45 g/ml. If the bulk density is less than 0.3 g/ml, then the flowability of the powder may be lowered, which is not be preferable for handling. If the bulk density is more than 0.5 g/ml, then the compressibility may be lowered.

The low-substituted hydroxypropylcellulose powder of the present invention can be used as a binder or a disintegrant of a solid dosage form such as a tablet or a granule. A tablet can be obtained using any production methods such as a dry direct tableting method, a wet agitation-granulation tableting method, a fluidized bed granulation tableting method, and a dry granulation tableting method.

Herein, the dry direct tableting method refers to a method in which a low-substituted hydroxypropylcellulose powder, a drug, and other ingredients such as a vehicle and a lubricant are dry-mixed and then tableting is performed. In this method, the production steps can be simplified because a granulating step is not included, and the productivity is high. The wet agitation-granulation tableting method refers to a method in which a low-substituted hydroxypropylcellulose powder, a drug, and other ingredients such as a vehicle are granulated with water or a water-soluble binder solution using a high-speed agitation granulating device, a powder obtained by drying the resultant and a lubricant are mixed, and then tableting is performed. This method provides high uniformity of the drug content. The fluidized bed granulation tableting method refers to a method in which a low-substituted hydroxypropylcellulose powder, a drug, and other ingredients such as a vehicle are granulated with water or a water-soluble binder solution using a fluidized bed granulating device, a powder obtained by drying the resultant and a lubricant are mixed, and then tableting is performed. This method provides high uniformity of the drug content, as in the wet agitation-granulation tableting method. The dry granulation tableting method refers to a method in which a low-substituted hydroxypropylcellulose powder, a drug, and other ingredients such as a vehicle are granulated by compression and then tableting is performed. This, method is effective for a drug that is sensitive to water or a solvent. Furthermore, this method can be applied also to oral rapidly disintegrating tablets that are rapidly disintegrated in the oral cavity without water or with a small amount of water, which have been actively developed recently. This method provides a dosage form that is effective for elderly and children having poor swallowing ability.

Moreover, the low-substituted hydroxypropylcellulose of the present invention can be used also as a binder or a disintegrant of a granule. A granule can be obtained using any production methods such as the wet agitation granulation, the fluidized bed granulation, and the dry granulation.

A cylindrical granule produced by extrusion granulation and a granulated matter after extrusion granulation can be spheroidized using a marumerizer. Furthermore, layering also can be performed in which a binder solution is sprayed in a state where a mixed powder of a low-substituted hydroxypropylcellulose powder, a drug powder, and other ingredients such as a vehicle is scattered over a spherical core made of sugars or the like.

There is no particular limitation on the drug used for producing a preparation from the low-substituted hydroxypropylcellulose powder of the present invention, and examples thereof include drugs for the central nervous system, drugs for the circulatory system, drugs for the respiratory system, drugs for the digestive system, antibiotics, chemotherapeutics, drugs for the metabolic system, and vitamin-based drugs.

Examples of the drugs for the central nervous system include diazepam, idevenone, aspirin, ibuprofen, paracetamol, naproxen, piroxicam, diclofenac, indomethacin, sulindac, lorazepam, nitrazepam, phenyloin, acetaminophen, ethenzamide, and ketoprofen.

Examples of the drugs for the circulatory system include molsidomine, vinpocetine, propranolol, methyldopa, dipyridamole, furosemide, triamterene, nifedipine, atenolol, spironolactone, metoprolol, pindolol, captopril, and isosorbide nitrate.

Examples of the drugs for the respiratory system include amlexanox, dextromethorphan, theophylline, pseudoephedrine, salbutamol, and guaifenesin.

Examples of the drugs for the digestive system include: benzimidazole-based drugs having an antiulcer action, such as 2-{[3-methyl-4-(2,2,2-trifluoroethoxy)-2-pyridyl]methylsulfinyl}benzimidazole, and 5-methoxy-2-[(4-methoxy-3,5-dimethyl-2-pyridyl)methylsulfinyl]benzimidazole; cimetidine; ranitidine; pancreatin; bisacodyl; and 5-aminosalicylic acid.

Examples of the antibiotics and the chemotherapeutics include cephalexin, cefaclor, cephradine, amoxicillin, pivampicillin, bacampicillin, dicloxacillin, erythromycin, erythromycin stearate, lincomycin, doxycycline, and trimethoprim/sulfamethoxazole.

Examples of the drugs for the metabolic system include serrapeptase, lysozyme chloride, adenosine triphosphate, glibenclamide, and potassium chloride.

Examples of the vitamin-based drugs include vitamin B1, vitamin B2, vitamin B6, and vitamin C.

Hereinafter, the present invention is described in detail by way of examples, but the present invention is not limited to these examples.

EXAMPLES

Example 1

First, 806 g of powdered pulp (750 g in an anhydrous state) was charged into a 10 L internally-agitating type reaction device, 303 g of 26%; by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.105. Next, nitrogen purge was performed, 123 g of propylene oxide (0.164 parts by weight with respect to cellulose) was added to the resultant, then the mixture was reacted at a jacket temperature of 60° C. for 1.5 hours, and thus 1232 g of hydroxypropylcellulose crude reaction product was obtained in which the molar substitution number of hydroxypropoxyl groups per anhydrous glucose unit was 0.28. The etherification efficiency was 61.4%.

Next, 236 g of 50% by weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 58.2% by weight. The dehydrated product was dried at 80° C. for one whole day and night in a shelf drier.

Figure 1:
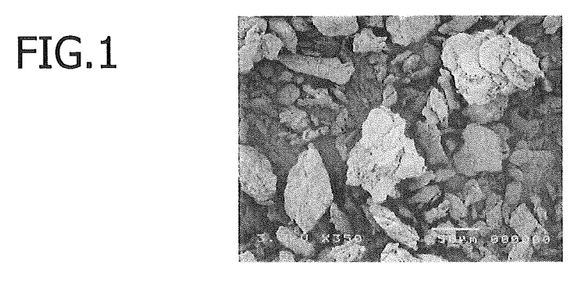
FIG. 1 shows an electron micrograph of a powder obtained in Example 1.

The dried product was pulverized using a batch-type planetary ball mill P-5 manufactured by FRITSH, at 255 rpm for 60 minutes. The pulverized product was sieved through a sieve with an opening of 180 μm, and thus the targeted low-substituted hydroxypropylcellulose powder was obtained. This powder was evaluated by the following method, in terms of average particle size, specific surface area, bulk density, repose angle, elastic recovery ratio, compressibility, swollen volume increase ratio, and swollen volume increase rate. Table 1 shows the results. FIG. 1 shows an electron micrograph of the obtained powder. FIG. 1 shows that the powder had lost a fibrous form with a smooth surface derived from the raw material pulp by compaction-grinding, had a constant shape, and contained voids.

The average particle size was measured using a HELOS&RODOS (manufactured by Sympatec) for measuring particle size distribution with laser diffractometry.

The specific surface area was measured using a MICROMERITICS GEMINI 2375 (manufactured by SHIMADZU CORPORATION).

The bulk density was obtained using a powder tester (manufactured by Hosokawa Micron Corporation), by uniformly and loosely (that is, without tapping) filling the sample from above (23 cm), through a sieve with 24 mesh according to JIS, into a 100 cc cylindrical vessel (made of stainless steel) with a diameter of 5.03 cm and a height of 5.03 cm, and then measuring the weight after leveling at the upper surface.

The repose angle was obtained using a powder tester (manufactured by Hosokawa Micron Corporation), by allowing the sample to flow from a height of 75 mm onto a disc-shaped stage with a size of 80 mm, and then measuring the angle formed by the deposited powder and the stage.

The elastic recovery ratio was calculated from the following equation, based on the thickness of a tablet obtained by compression the sample powder in a tablet weight of 480 mg and at a compression force of 50 MPa, using a tableting tester (manufactured by SANKYO PIO-TECH. CO., Ltd.) with a flat punch for a tablet diameter of 11.3 mm.

Elastic recovery ratio={(tablet thickness after 30 seconds−minimum tablet thickness)/(minimum tablet thickness)}×100

The compressibility was obtained by measuring the hardness of a tablet obtained by compression the powder in a tablet weight of 480 mg and at a compression force of 150 MPa, using a tableting tester (manufactured by SANKYO PIO-TECH. CO., Ltd.) with a flat shape for a tablet diameter of 11.3 mm.

The swollen volume increase ratio was obtained by molding the powder at a compression force of 1 t into a tablet having a flat face with a diameter of 15 mm, dropping water thereonto, and then measuring the volume increase ratio after 10 minutes at which the tablet had been swollen by absorbing the water.

The swollen volume increase rate was calculated, by molding the powder at a compression force of 1 t into a tablet having a flat face with a diameter of 15 mm, dropping water thereonto, obtaining the swollen volume increase ratio based on a change in the volume after 30 seconds at which the tablet had been swollen, and then performing the calculation based on this ratio.

Next, using the obtained powder, an ascorbic acid tablet was produced by direct tableting under the following conditions.

Tablet Composition:
  ascorbic acid granulated powder VC-97 (manufactured by BASF Takeda Vitamins Ltd.): 90 parts by weight
  low-substituted hydroxypropylcellulose;
    10 parts by weight
  magnesium stearate: 0.5 parts by weight
Tableting machine: rotary tableting machine (manufactured by Kikusui Seisakusho Ltd.)
Tablet size: diameter 8 mm, radius of curved face 6.5 mm
Tablet weight: 200 mg
Tableting pressure:
  main-pressure 0.5 t,
  pre-pressure 0.2 t
Tableting speed: 40 rpm The tablet hardness, the disintegration time (test fluid: water) in Disintegration Test according to Japanese Pharmacopoeia, and the tablet weight variation, of the obtained tablet were measured. Table 1 shows the results.

Example 2

First, 806 g of powdered pulp (750 g in an anhydrous state) was charged into a 10 L internally-agitating type reaction device, 504 g of 26% by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.175. Next, nitrogen purge was performed, 143 g of propylene oxide (0.190 parts by weight with respect to cellulose) was added to the resultant, then the mixture was reacted at a jacket temperature of 60° C. for 1.5 hours, and thus 1453 g of hydroxypropylcellulose crude reaction product was obtained in which a molar substitution number of hydroxypropoxyl groups per anhydrous glucose unit was 0.29. The etherification efficiency was 53.6%.

Next, 394 g of 50% by weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 60.5% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The pulverized product was sieved through a sieve with an opening of 180 μm, and thus the targeted low-substituted hydroxypropylcellulose powder was obtained. This powder was evaluated as in Example 1, in terms of average particle size, specific surface area, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Example 3

First, 806 g of powdered pulp (750 g in an anhydrous state) was charged into a 10 L internally-agitating type reaction device, 808 g of 26% by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.280. Next, nitrogen purge was performed, 173 g of propylene oxide (0.230 parts by weight with respect to cellulose) was added to the resultant, then the mixture was reacted at a jacket temperature of 60° C. for 1.5 hours, and thus 1787 g of hydroxypropylcellulose crude reaction product was obtained in which a molar substitution number of hydroxypropoxyl groups per anhydrous glucose unit was 0.30. The etherification efficiency was 46.4%.

Next, 629 g of 50% by weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 62.2% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The pulverized product was sieved through a sieve with an opening of 180 μm, and thus the targeted low-substituted hydroxypropylcellulose powder was obtained. This powder was evaluated as in Example 1, in terms of average particle size, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Example 4

First, 8.6 kg of powdered pulp (8 kg in an anhydrous state) was charged into a 130 L internally-agitating type reaction device, 3.5 kg of 35% by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.151. Next, nitrogen purge was performed, 1.6 kg of propylene oxide (0.2 parts by weight with respect to cellulose) was added to the resultant, then the mixture was reacted at a jacket temperature of 60° C. for 1.5 hours, and thus 13.7 kg of hydroxypropylcellulose crude reaction product was obtained in which a molar substitution number of hydroxypropoxyl groups per anhydrous glucose unit was 0.35.

Next, 11.8, kg of 50% by weight acetic acid was added and mixed in the internally-agitating type reaction device, thereby performing neutralization. The neutralized product was washed in hot water at 90° C., using a batch-type suction filtration machine. The water content of the dehydrated product was 59.5% by weight. The dehydrated product was dried at an air intake temperature of 80° C. in a fluidized bed drier until the discharge air temperature was 60° C. The etherification efficiency was 57.6%.

The dried product was pulverized and dehydrated, using a roller mill IS-250 manufactured by IHI, at an applied pressure of 3 MPa, a table rotational speed of 120 rpm, a classification rotational speed of 300 rpm, a gas volume of 11 Nm$^3$/min, and a supply time of 5 kg/hr. The pulverized product was sieved through a sieve with an opening of 75 μm, and thus the targeted low-substituted hydroxypropylcellulose powder was obtained.

This powder was evaluated as in Example 1, in terms of average particle size, specific surface area, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Example 5

First, 806 g of powdered pulp (750 g in an anhydrous state) was charged into a 10 L internally-agitating type reaction device, 303 g of 26% by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.105. Next, nitrogen purge was performed, 81.8 g of propylene oxide (0.109 parts by weight with respect to cellulose) was added to the resultant, then the mixture was reacted at a jacket temperature of 60° C. for 1 hour, and thus 1190.8 g of hydroxypropylcellulose crude reaction product was obtained in which a molar substitution number of hydroxypropoxyl groups per anhydrous glucose unit was 0.20. The etherification efficiency was 65.0%.

Next, 2250 g of warm water at 50° C. and 59 g of glacial acetic acid were put into a 10 L batch-type kneader, and the entire 1190.8 g of the crude reaction product was loaded thereinto and dissolved. It took 20 minutes for the crude reaction product to be completely dissolved. Then, 118 g of 50% by weight acetic acid was added at a rate of 20 g/min, thereby performing neutralization. The neutralized product was washed in hot water at 90° C. and dehydrated, using a batch-type centrifuge at a rotational speed of 3000 rpm. The water content of the dehydrated product was 62.2% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The pulverized product was sieved through a sieve with an opening of 75 μm, and thus the targeted low-substituted hydroxypropylcellulose powder was obtained. This powder was evaluated as in Example 1, in terms of average particle size, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Comparative Example 1

First, 806 g of powdered pulp (750 g in an anhydrous state) was charged into a 10 L internally-agitating type reaction device, 300 g of 13% by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.052. Next, nitrogen purge was performed, 146 g of propylene oxide (0.195 parts by weight with respect to cellulose) was added to the resultant, then the mixture was reacted at a jacket temperature of 60° C. for 1.5 hours, and thus 1252 g of hydroxypropylcellulose crude reaction product was obtained in which a molar substitution number of hydroxypropoxyl groups per anhydrous glucose unit was 0.28. The etherification efficiency was 50.9%.

Next, 117 g of 50% weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 50.1% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The pulverized product was sieved through a sieve with an opening of 180 μm, and thus the targeted low-substituted hydroxypropylcellulose powder was obtained. This powder was evaluated as in Example 1, in terms of average particle size, specific surface area, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Comparative Example 2

First, 806 g of powdered pulp (750 g in an anhydrous state) was charged into a 10 L internally-agitating type reaction device, 761 g of 35% by weight sodium hydroxide was charged into the reaction device, then mixing was performed at 45° C. for 30 minutes, and thus alkali cellulose was obtained in which the weight ratio of sodium hydroxide with respect to anhydrous cellulose was 0.355. Next, nitrogen purge was performed, 161 g of propylene oxide (0.214 parts by weight with respect to cellulose) was added to the resultant, then the mixture was reacted at a jacket temperature of 60° C. for 1.5 hours, and thus 1728 g of hydroxypropylcellulose crude reaction product was obtained in which the molar substitution number of hydroxypropoxyl groups per anhydrous glucose unit was 0.28. The etherification efficiency was 43.5%.

Next, 800 g of 50% by weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 65.2% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The pulverized product was sieved through a sieve with an opening of 180 μm, and thus the targeted low-substituted hydroxypropylcellulose powder was obtained. This powder was evaluated as in Example 1, in terms of average particle size, specific surface area, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Comparative Example 3

First, 806 g of powdered pulp (750 g in an anhydrous state) was charged into a 10 L internally-agitating type reaction device, 844 g of 43% by weight sodium hydroxide solution was charged into the reaction device, then mixing was performed at 45° C. for 30 minutes, and this alkali cellulose was obtained in which the weight ratio of sodium hydroxide with respect to anhydrous cellulose was 0.484. Next, nitrogen purge was performed, 165 g of propylene oxide (0.220 parts by weight with respect to cellulose) was added to the resultant, then the mixture was reacted at a jacket temperature of 60° C. for 1.5 hours, and thus 1815 g of hydroxypropylcellulose crude reaction product was obtained in which a molar substitution number of hydroxypropoxyl groups per anhydrous glucose unit was 0.27. The etherification efficiency was 42.3%.

Next, 1088 g of 50% by weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 66.8% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The pulverized product was sieved through a sieve with an opening of 180 μm, and thus the targeted low-substituted hydroxypropylcellulose powder was obtained. This powder was evaluated as in Example 1, in terms of average particle size, specific surface area, bulk density, repose angle, elastic recovery ratio, compressibility, swollen volume increase ratio, and swollen volume increase rate. Table 1 shows the results.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results.

Comparative Example 4

Sheet-shaped pulp was immersed in a 43% sodium hydroxide solution and then squeezed, and thus alkali cellulose was obtained in which 22.2% by weight sodium hydroxide was contained and the weight ratio of sodium hydroxide with respect to anhydrous cellulose was 0.484. The obtained alkali cellulose was cut into chips with a size of approximately 1 cm squares, and the alkali cellulose in an amount of 350 g expressed in terms of cellulose was charged into a reaction device with a volume of 5 L. Then, nitrogen purge was performed. Next, 79 g of propylene oxide (0.226 parts by weight with respect to cellulose) was added to the resultant, then the mixture was reacted at a jacket temperature of 45° C. for 2 hours and 65° C. for 30 minutes, and thus 857 g of hydroxypropylcellulose crude reaction product was obtained in which a molar substitution number of hydroxypropoxyl groups per anhydrous glucose unit was 0.27. The etherification efficiency was 42.0%.

Next, as in Japanese Patent Application Examined Publication No. 57-53100/1982 and Japanese Patent Application Unexamined Publication No. 10-305084/1998, a part of the crude reaction product was dissolved in hot water and then neutralized (partial neutralization), the obtained dried product was pulverized by impact milling, and thus a sample was obtained.

Next, 1750 g of water at 50° C. and 52 g of glacial acetic acid were put into a 5 L batch-type kneader, and the entire 857 g of the crude reaction product was loaded thereinto and dissolved. It took 30 minutes for the crude reaction product to be completely dissolved. Then, 633 g of 33% acetic acid was added at a rate of 20 g/min, thereby performing neutralization and precipitation.

The neutralized product was washed in hot water at 90° C., using a batch-type centrifuge at a rotational speed of 3000 rpm. The water content of the dehydrated product was 75.4% by weight. The dehydrated product was dried at 80° C. for one whole day and night in a fan oven.

The obtained dried product was pulverized using a high-rotation impact-type mill Victory Mill having a screen with an opening of 0.3 mm. The pulverized product was sieved through a sieve with an opening of 75 μm, and thus the targeted low-substituted hydroxypropylcellulose powder was obtained. This powder was evaluated as in Example 1, in terms of average particle size, specific surface area, bulk density, repose angle, elastic recovery ratio, compressibility, swollen volume increase ratio, and swollen volume increase rate. Table 1 shows the results.

Figure 2:
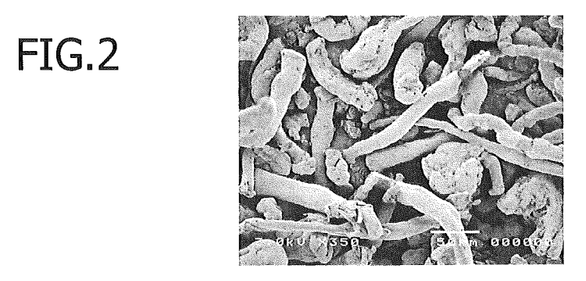
FIG. 2 shows an electron micrograph of a powder obtained in Comparative Example 4.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results. FIG. 2 shows an electron micrograph of the obtained powder. FIG. 2 shows that the powder contained fibrous substances with a smooth surface derived from the raw material pulp, and dense spherical particles generated in the dissolution step, in a mixed manner.

Comparative Example 5

After the complete dissolution described in Japanese Patent Application Unexamined Publication No. 11-322802/1999, neutralization was performed, the obtained dried product was pulverized by impact milling, and thus a sample was obtained.

Next, 2450 g of water at 50° C. was put into a 5 L batch-type kneader, and the entire 857 g of the crude reaction product reacted as in Example 4 was loaded thereinto and dissolved (completely dissolved). It took one hour for the crude reaction product to be completely dissolved. Then, 793 g of 33% acetic acid was added at a rate of 20 g/min, thereby performing neutralization and precipitation.

The neutralized product was washed in hot water at 90° C. and dehydrated, using a batch-type centrifuge at a rotational speed of 3000 rpm. The water content of the dehydrated product was 80.1% by weight. The dehydrated product was dried at 80° C. for one whole day and night in a fan oven.

The obtained dried product was pulverized using a high-rotation impact-type mill Victory Mill having a screen with an opening of 0.3 mm. The pulverized product was sieved through a sieve with an opening of 75 μm, and thus the targeted low-substituted hydroxypropylcellulose powder was obtained. This powder was evaluated as in Example 1, in terms of average particle size, bulk density, repose angle, elastic recovery ratio, compressibility, swollen volume increase ratio, and swollen volume increase rate. Table 1 shows the results.

Figure 3:
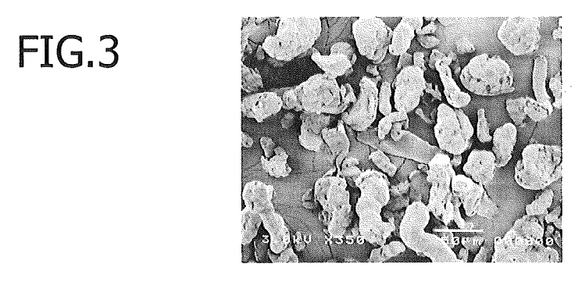
FIG. 3 shows an electron micrograph of a powder obtained in Comparative Example 5.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results. FIG. 3 shows an electron micrograph of the obtained powder. FIG. 3 shows that the powder was constituted by a smaller amount of fibrous particles generated in the dissolution step, and dense spherical particles.

Comparative Example 6

A low-substituted hydroxypropylcellulose powder was obtained as in Example 2, except that a high-rotation impact-type mill Victory Mill having a screen with an opening of 0.3 mm was used. This powder was evaluated as in Example 1, in terms of average particle size, specific surface area, bulk density, repose angle, elastic recovery ratio, compressibility, swollen volume increase ratio, and swollen volume increase rate. Table 1 shows the results.

Figure 4:
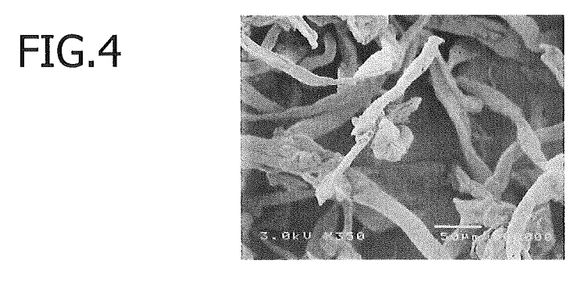
FIG. 4 shows an electron micrograph of a powder obtained in Comparative Example 6.

Furthermore, an ascorbic acid tablet was produced by direct tableting as in Example 1. The tablet hardness, the disintegration time (test fluid: water) in Disintegration Test according to Japanese Pharmacopoeia, and the tablet weight variation, of the obtained tablet were measured. Table 1 shows the results. FIG. 4 shows an electron micrograph of the obtained powder. FIG. 4 shows that the powder was in the form of fibers with a smooth surface derived from the raw material pulp.

Figure 5:
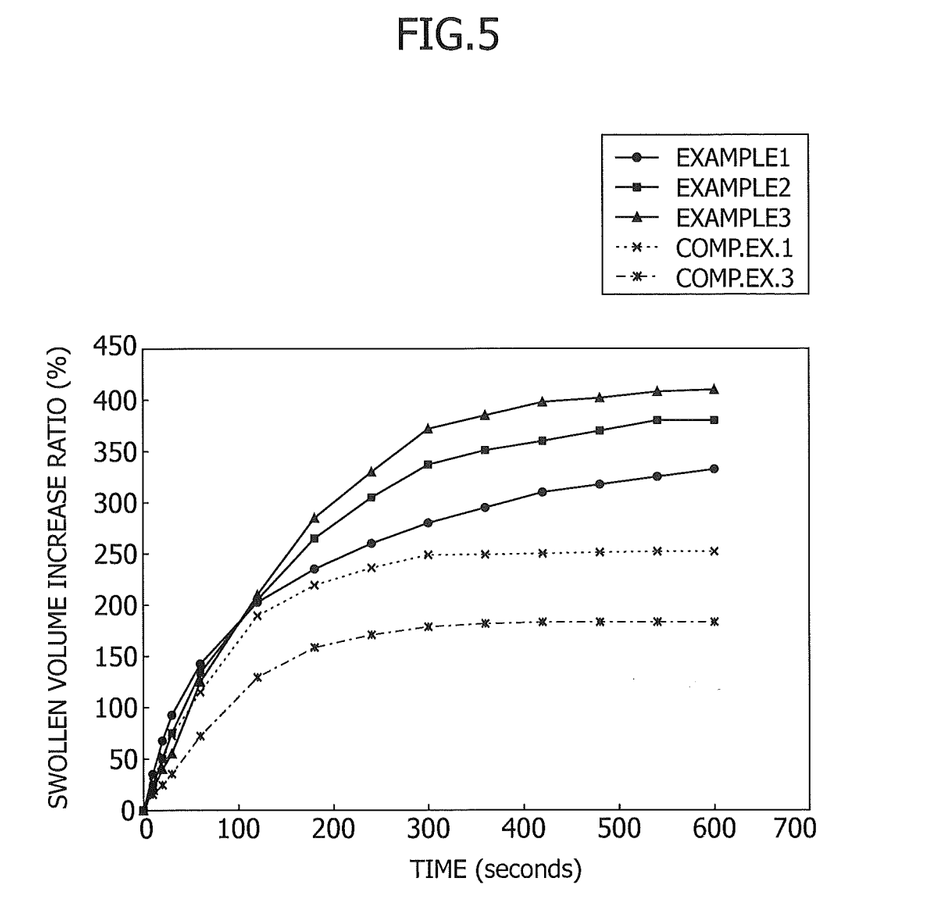
FIG. 5 shows the time-series swollen volume increase ratio, of powders obtained in Examples 1 to 3 and Comparative Examples 1 and 3.

FIG. 5 shows the results obtained by observing the influence on the swelling properties, given by the weight ratio of the sodium hydroxide with respect to the anhydrous cellulose in the alkali cellulose. In FIG. 5, the horizontal axis indicates the measurement time after starting the addition of water, and the vertical axis indicates the swollen volume increase ratio.

It is shown that in the examples, both of the swollen volume increase ratio and the swollen volume increase rate are larger than those in the comparative examples.

TABLE 1

| | production conditions | | | | | | powder properties | | |
|---|---|---|---|---|---|---|---|---|---|
| | | | | | water | | | | |
| | shape of pulp | weight ratio of NaOH | weight ratio of NaOH (mol) | esterification efficiency (%) | content of dehydrated product (%) | pulverization method | average particle size (μm) | specific surface area (m2/g) | bulk density (g/ml) |
| Example 1 | powder | 0.105 | 0.28 | 61.4 | 58.2 | compaction-grind | 42 | 1.21 | 0.42 |
| Example 2 | powder | 0.175 | 0.29 | 53.6 | 60.5 | compaction-grind | 44 | 1.12 | 0.44 |
| Example 3 | powder | 0.28 | 0.3 | 46.4 | 62.2 | compaction-grind | 43 | 1.05 | 0.45 |
| Example 4 | powder | 0.151 | 0.35 | 57.6 | 59.5 | compaction-grind | 51 | 1.18 | 0.42 |
| Example 5 | powder | 0.105 | 0.2 | 65 | 62.2 | compaction-grind | 35 | 1.01 | 0.48 |
| Comp. Ex. 1 | powder | 0.052 | 0.28 | 50.9 | 50.1 | compaction-grind | 44 | 0.92 | 0.44 |
| Comp. Ex. 2 | powder | 0.355 | 0.28 | 43.5 | 65.2 | compaction-grind | 41 | 0.9 | 0.46 |
| Comp. Ex. 3 | powder | 0.484 | 0.27 | 42.3 | 66.8 | compaction-grind | 40 | 0.88 | 0.41 |
| Comp. Ex. 4 | sheet | 0.484 | 0.27 | 42 | 75.4 | impact-milling | 45 | 0.75 | 0.38 |
| Comp. Ex. 5 | sheet | 0.484 | 0.27 | 42 | 80.1 | impact-milling | 42 | 0.45 | 0.49 |
| Comp. Ex. 6 | powder | 0.175 | 0.29 | 53.6 | 60.5 | impact-milling | 65 | 0.81 | 0.17 |

| | powder properties | | | | | ascorbic acid tablet by direct tableting | | |
|---|---|---|---|---|---|---|---|---|
| | flowability | elastic | compressibility | swollen volume | swollen volume | | | |
| | response angle (°) | recovery ratio (%) | tablet hardness (kgf) | increase ratio (%) | increase rate (%/mim) | hardness (kgf) | disintegration time (min) | weight deviation (CV %) |
| Example 1 | 37 | 3.8 | 42 | 330 | 190 | 4.1 | 2.2 | 0.6 |
| Example 2 | 37 | 4.1 | 45 | 380 | 150 | 4.2 | 2.4 | 0.5 |
| Example 3 | 38 | 4.5 | 41 | 410 | 110 | 4 | 2.3 | 0.5 |
| Example 4 | 39 | 4.5 | 43 | 502 | 130 | 4.5 | 2.3 | 0.3 |
| Example 5 | 36 | 4.2 | 36 | 301 | 270 | 3.8 | 1.8 | 0.5 |
| Comp. Ex. 1 | 39 | 3.8 | 35 | 250 | 200 | 3.5 | 3.8 | 0.6 |
| Comp. Ex. 2 | 39 | 6.8 | 32 | 260 | 82 | 3.3 | 4.2 | 0.3 |
| Comp. Ex. 3 | 39 | 8.1 | 31 | 180 | 50 | 3.2 | 4.6 | 0.3 |
| Comp. Ex. 4 | 45 | 8.7 | 25 | 290 | 85 | 2.5 | 2.4 | 0.9 |
| Comp. Ex. 5 | 39 | 9.5 | 10 | 500 | 250 | 1.8 | 0.5 | 0.6 |
| Comp. Ex. 6 | 55 | 13.1 | 31 | 310 | 180 | 3.1 | 3 | 2.2 |

* Weight ratio of sodium hydroxide with respect to anhydrous cellulose in alkali cellulose As clearly shown in Table 1, in a case where sodium hydroxide in a predetermined weight ratio was contained and compaction-grinding was used, the specific surface area increased, and the elastic recovery ratio was reduced, and thus the compressibility increased. Accordingly, when a preparation was produced from this powder, a tablet with high tablet hardness was obtained. Furthermore, the swollen volume increase ratio and the swollen volume increase rate increased. Thus, when a preparation was produced from this powder, a preparation with short disintegration time was obtained. On the other hand, the results of Comparative Examples 1 to 3 show that in a case where compaction-grinding was used but sodium hydroxide in a predetermined weight ratio was not contained, an obtained powder was poor in specific surface area, compressibility, swollen volume increase ratio, which is an important swelling property as a disintegrant, tablet hardness, and disintegration time. Furthermore, in the results of Comparative Examples 2 and 3, the swollen volume increase rate, which is an important swelling property as a disintegrant, was also poor. The results of Comparative Example 6 show that in a case where sodium hydroxide in a predetermined weight ratio was contained but impact milling was used instead of compaction-grinding, an obtained powder was poor in specific surface area, flowability, compressibility, tablet hardness, and disintegration time, and had large weight variation. In Comparative Example 4, sheet-shaped pulp was used, and thus alkali cellulose containing an excessive amount of sodium hydroxide was used, so that the swollen volume increase rate was poor. Moreover, since an impact-type mill was used, the specific surface area was small, the elastic recovery ratio was large, and the compressibility was low. On the other hand, in Comparative Example 5, the amount of fibrous was small due to complete dissolution, and thus the repose angle was small, and the flowability was excellent, but the compressibility was low.

1) Orally Disintegrating Tablet

Example 6

Using the low-substituted hydroxypropylcellulose obtained by the method described in Example 1, an oral rapidly disintegrating tablet was produced under the following conditions.

Tablet composition:
  erythritol (sieved through 250 μm sieve):
    70 parts by weight
  low-substituted hydroxypropylcellulose:
    30 parts by weight
  magnesium stearate: 0.5 parts by weight
Tableting machine: single tableting machine, tableting tester (manufactured by SANKYO PIO-TECH. CO., Ltd.)
Tablet size: diameter 11.3 mm, flat shape
Tableting pressure: 10, 25, 50 MPa The obtained tablet was evaluated, in terms of tablet hardness, orally disintegration time, and feeling in use. As the orally disintegration time, tablets were simply put into the mouths of four healthy adults without being chewed in the oral cavities, the time taken for the tablets to be completely dissolved or disintegrated was measured, and an average value thereof was calculated. Table 2 shows the results of the tablet hardness and the orally disintegration time.

Comparative Example 7

An oral rapidly disintegrating tablet was produced as in Example 6, except that the low-substituted hydroxypropylcellulose obtained by the method described in Comparative Example 4 was used. The obtained tablet was evaluated as in Example 6. Table 2 shows the results.

TABLE 2

| tableting pressure | tablet hardness (N) | | oral disintegration time of tablet (sec) | |
| --- | --- | --- | --- | --- |
| (MPa) | Example 6 | Comp. Ex. 7 | Example 6 | Comp. Ex. 7 |
| 10 | 33 | 18 | 18 | 24 |
| 25 | 42 | 28 | 20 | 29 |
| 50 | 70 | 60 | 29 | 35 |

Example 6 exhibited higher tablet hardness, and required shorter disintegration time in the oral cavity, than those in Comparative Example 7. In Example 6, none of the tablets had a rough surface, and thus creamy feeling in use was provided. On the other hand, Comparative Example 7 provided bad feeling in use as if paper had been put into the mouth.

2) Wet-Agitation Granulation

Example 7

Using the low-substituted hydroxypropylcellulose obtained by the method described in Example 4, wet agitation granulation was performed, by charging a powder having the following composition into a vertical granulator FM-VG-05 (manufactured by POWREX CORPORATION), performing preliminary mixing for one minute at a main shaft rotational speed of 600 rpm and a chopper rotational speed of 1000 rpm, adding 55 g of water, and then performing mixing for five minutes.

Tablet Composition:
  Ethenzamide: 210 g (70 parts by weight)
  200#lactose: 60 g (20 parts by weight)
  low-substituted hydroxypropylcellulose:
    30 g (10 parts by weight)

The granulated matter was sieved through a sieve with an opening of 1180 μm, and then dried at an air intake temperature of 60° C. and an air flow volume of 70 m³/hr in a fluidized bed drier until the discharge air temperature was 45° C.

Table 3 shows the average particle size, the bulk density, the tap density, the degree of compression, and the repose angle of the obtained granule.

It should be noted that the average particle size, the bulk density, and the repose angle of the obtained granule were measured as in the low-substituted hydroxypropylcellulose powder, and the tap density and the degree of compression were measured by the following method.

More specifically, tap density refers to the bulk density in a tightly filled state obtained by performing tapping on a vessel in a state in which the bulk density can be measured. The tapping refers to an operation to make a sample be tightly filled, by repeatedly dropping the vessel filled with the sample from a predetermined height thereby providing the bottom portion with a light impact. Thus, the tap density can be measured in the following manner: when weighing has been completed after leveling at the upper surface in the measurement of the bulk density, a cap (a component of a powder tester manufactured by Hosokawa Micron Corporation) is placed on the vessel, powder is added to the upper edge of the cap, and tapping is performed 180 times at a tapping height of 1.8 cm, and when the tapping has been completed, the cap is removed and weighing is performed after leveling the powder at the upper surface of the vessel. These operations are performed using a powder tester (PT-D) manufactured by Hosokawa Micron Corporation.

Herein, the degree of compression refers to the degree of volume decreased, and is calculated from the following equation.

Degree of compression(%)=[(tap density−bulk density)/tap density]×100

Next, 0.5 parts by weight of magnesium stearate was added and then mixed with 100 parts by weight of the granule, and thus a powder for tableting was obtained. Using this powder, continuous tableting was performed under the following conditions.

Tableting machine: rotary tableting machine (manufactured by Kikusui Seisakusho Ltd.)
Tablet size: diameter 8 mm, radius of curvature 6.5 mm, tablet weight 200 mg
Tableting pressure: main-pressure 1 t, pre-pressure 0.2 t
Tableting speed: 40 rpm The obtained tablet was evaluated, in terms of tablet hardness, disintegration time (test fluid: water) in Disintegration Test according to Japanese Pharmacopoeia, tablet friability measured as below following Friability Test according to Japanese Pharmacopoeia, occurrence of capping measured by the number of tablets in which capping occurred after Friability Test, and tablet weight variation.

In Friability Test, after the test was performed for 16 minutes using a friability test apparatus described in Japanese Pharmacopoeia on 20 tablets at 25 rpm, the ratio of weight lost was calculated from the following equation.

[{(tablet weight before test)−(tablet weight after test)}/(tablet weight before test)]×100

The occurrence of capping was calculated, based on the number of tablets that were broken into two layers, after Friability Test above.

The tablet weight deviation was obtained by measuring the weight of 20 tablets and calculating their coefficient of variation (CV value).

Table 4 shows the obtained results.

Comparative Example 8

Wet agitation granulation was performed as in Example 7, except that the low-substituted hydroxypropylcellulose obtained by the method described in Comparative Example 4 was used. Table 3 shows the average particle size, the bulk density, the tap density, the degree of compression, and the repose angle of the obtained granule.

Next, continuous tableting was performed as in Example 7, and the resultant was evaluated. Table 4 shows the results.

Comparative Example 9

Wet agitation granulation was performed as in Example 7, except that microcrystalline cellulose Ceolus PH-101 (manufactured by Asahi Kasei Chemicals) was used instead of the low-substituted hydroxypropylcellulose. Herein, since microcrystalline cellulose has water retentivity lower than that of low-substituted hydroxypropylcellulose, water was reduce to 36 g. Table 3 shows the average particle size, the bulk density, the tap density, the degree of compression, and the repose angle of the obtained granule.

Next, continuous tableting was performed as in Example 7, and the resultant was evaluated. Table 4 shows the results.

TABLE 3

| | average particle size (μm) | bulk desity (g/ml) | tap desity (g/ml) | degree of compression (%) | repose angle (*) |
|---|---|---|---|---|---|
| Example 7 | 96.1 | 0.512 | 0.676 | 24.3 | 36 |
| Comp. Ex. 8 | 96.7 | 0.479 | 0.703 | 31.9 | 41 |
| Comp. Ex. 9 | 95.3 | 0.494 | 0.679 | 27.2 | 39 |

In Example 7, the bulk density was higher and the weight was heavier, and the degree of compression and the repose angle were smaller than those of Comparative Examples 8 and 9, and thus a granule with excellent flowability was obtained.

TABLE 4

| | tablet hardness (N) | disintegration time of tablet (min) | weight loss of tablet (%) | occurrence of capping (%) | tablet weight deviation (CV %) |
|---|---|---|---|---|---|
| Example7 | 94 | 2.1 | 0.53 | 0 | 0.52 |
| Comp. Ex. 8 | 53 | 0.9 | 0.63 | 0 | 1.1 |
| Comp. Ex. 9 | 44 | 9.2 | 2.5 | 40 | 0.76 |

In Example 7, an excellent preparation was obtained in which the tablet hardness was higher and the tablet weight variation was lower than those of Comparative Example 8. In Comparative Example 9 in which microcrystalline cellulose was used, capping occurred, the tablet friability was high, and the tablet hardness was low, but a preparation in Example 7 was excellent in all of the evaluation items.

3) Fluidized Bed Granulation

Example 8

Using the low-substituted hydroxypropylcellulose obtained by the method described in Example 1, granulation was performed, by charging a powder having the following composition into a fluidized bed granulating device Multiplex MP-01 (manufactured by POWREX CORPORATION), and spraying 60 g of an aqueous 5% by weight solution of hydroxypropylmethylcellulose TC-5R (manufactured by Shin-Etsu Chemical Co., Ltd.) at a rate of 10 g/min, at an air intake temperature 60° C., an air flow volume of 50 m³/hr, and a discharge air temperature of 30 to 35° C.

Tablet Composition:
Acetaminophen: 80 g (40 parts by weight)
200#lactose: 28 g (14 parts by weight)
Cornstarch: 12 g (6 parts by weight)
low-substituted hydroxypropylcellulose: 80 g (40 parts by weight)

Table 5 shows the average particle size, the bulk density, the tap density, the degree of compression, and the repose angle of the obtained granule.

Next, 0.5 parts by weight of magnesium stearate was added and then mixed with 100 parts by weight of the granule, and thus a powder for tableting was obtained. Using this powder, continuous tableting was performed as in Example 7. The obtained tablet was evaluated, in terms of tablet hardness, disintegration time (test fluid: water) in Disintegration Test according to Japanese Pharmacopoeia, and tablet weight variation. Table 6 shows the results.

Comparative Example 10

Fluidized bed granulation was performed as in Example 8, except that the low-substituted hydroxypropylcellulose obtained by the method described in Comparative Example 4 was used. Table 5 shows the average particle size, the bulk density, the tap density, the degree of compression, and the repose angle of the obtained granule.

Next, continuous tableting was performed as in Example 8, and the resultant was evaluated. Table 6 shows the results.

Comparative Example 11

Fluidized bed granulation was performed as in Example 8, except that the low-substituted hydroxypropylcellulose obtained by the method described in Comparative Example 5 was used. Table 5 shows the average particle size, the bulk density, the tap density, the degree of compression, and the repose angle of the obtained granule.

Next, continuous tableting was performed as in Example 8, and the resultant was evaluated. Table 6 shows the results.

TABLE 5

|  | average Particle size (μm) | bulk density (g/ml) | tap density (g/ml) | degree of compression (%) | repose angle (o) |
| --- | --- | --- | --- | --- | --- |
| Example 8 | 150 | 0.249 | 0.344 | 27.6 | 39 |
| Comp. Ex. 10 | 155 | 0.159 | 0.246 | 35.4 | 48 |
| Comp. Ex. 11 | 162 | 0.188 | 0.27 | 30.4 | 42 |

In Example 8, the bulk density was higher and the weight was heavier, and the degree of compression and the repose angle were smaller than those of Comparative Examples 10 and 11, and thus a granule with excellent flowability was obtained.

TABLE 6

|  | tablet hardness (N) | disintegration time of tablet (min) | tablet weight deviation (CV %) |
| --- | --- | --- | --- |
| Example 8 | 101 | 1 | 0.52 |
| Comp. Ex. 10 | 69 | 0.7 | 1.1 |
| Comp. Ex. 11 | 37 | 0.5 | 0.6 |

In Example 8, an excellent preparation was obtained in which the tablet hardness was higher and the tablet weight variation was smaller than those of Comparative Examples 10 and 11.

4) Extrusion Granulation

Example 9

Using the low-substituted hydroxypropylcellulose obtained by the method described in Example 4, wet agitation granulation was performed, by charging a powder having the following composition into a vertical granulator FM-VG-05 (manufactured by POWREX CORPORATION), performing preliminary mixing for one minute at a main shaft rotational speed of 600 rpm and a chopper rotational speed of 1000 rpm, adding 50 g of water, and then performing mixing for five minutes.

Tablet composition:
  Aspirin: 279 g (93 parts by weight)
  low-substituted hydroxypropylcellulose:
    15 g (5 parts by weight)
  hydroxypropylmethylcellulose TC-5E:
    6 g (2 parts by weight)

Next, extrusion granulation of the wet powder was performed using an extrusion granulator Dome Gran (manufactured by DALTON CORPORATION) with a 1.0 mm φ screen. Table 7 shows the granulating speed expressed in terms of a solid content. Furthermore, the obtained extrusion-granulated matter was spheroidized using a marumerizer (manufactured by DALTON CORPORATION) at 750 rpm. Then, the resultant was dried at an air intake temperature of 60° C. and an air flow volume of 70 m³/hr in a fluidized bed drier until the discharge air temperature was 45° C. The obtained granule was evaluated in terms of granule strength, and disintegration time (test fluid: water) in Disintegration Test according to Japanese Pharmacopoeia. Table 7 shows the results.

The granule strength was calculated from the following equation as the ratio of weight lost, after charging 10 g of the granules and 20 glass beads having a diameter of 5 mm into a friability test apparatus described in Japanese Pharmacopoeia, and performing the test for 4 minutes at 25 rpm.

[{(granule weight before test)−(granule weight after test)}/(granule weight before test)]×100

Comparative Example 12

Extrusion granulation was performed as in Example 9, except that the low-substituted hydroxypropylcellulose obtained by the method described in Comparative Example 4 was used. Table 7 shows the granulating speed expressed in terms of a solid content. The obtained wet-granulated matter was spheroidized and dried as in Example 9.

The obtained granule was evaluated in terms of granule strength, and disintegration time (test fluid: water) in Disintegration Test according to Japanese Pharmacopoeia. Table 7 shows the results.

TABLE 7

|  | granulating speed (g/min) | granule strength (%) | disintegration time of granule (min) |
| --- | --- | --- | --- |
| Example 9 | 274.6 | 0.7 | 0.8 |
| Comp. Ex. 12 | 108.6 | 2.1 | 0.6 |

In Example 9, an excellent preparation was obtained in which the granulating speed was faster, the productivity was higher, and the granule strength of the obtained granule was higher than those of Comparative Example 12.

5) Dry Granulation

Example 10

Using the low-substituted hydroxypropylcellulose obtained by the method described in Example 4, dry granulation was performed on a powder having the following composition, with a roller compactor MINI (manufactured by FREUND), at a roll pressure of 4 MPa, a roll rotational speed of 5 rpm, and a screw rotational speed of 12 rpm.

Tablet Composition:
  ascorbic acid: 50 g (10 parts by weight)
  200#lactose: 245 g (49 parts by weight)
  Cornstarch: 105 g (21 parts by weight)
  low-substituted hydroxypropylcellulose:
    100 g (20 parts by weight)
  magnesium stearate: 2.5 g (0.5 parts by weight)

The granulated matter was sieved through a sieve with an opening of 250 μm, and continuous tableting was performed with granulated matter under the following conditions.

Tableting machine: rotary tableting machine (manufactured by Kikusui Seisakusho Ltd.)
Tablet size: diameter 8 mm, radius of curvature 6.5 mm
Tablet weight: 200 mg
Tableting pressure: main-pressure 1 t, pre-pressure 0.2 t
Tableting speed: 40 rpm The obtained tablet was evaluated, in terms of tablet hardness, and disintegration time (test fluid: water) in Disintegration Test according to Japanese Pharmacopoeia. Table 8 shows the results.

Comparative Example 13

Dry granulation was performed as in Example 10, except that the low-substituted hydroxypropylcellulose obtained by the method described in Comparative Example 4 was used. Continuous tableting was performed as in Example 10. The obtained tablet was evaluated, in terms of tablet hardness, and disintegration time (test fluid: water) in Disintegration Test according to Japanese Pharmacopoeia. Table 8 shows the results.

TABLE 8

|  | tablet hardness (N) | tablet disintegration time (min) |
|---|---|---|
| Example 10 | 60 | 1.1 |
| Comp. Ex. 13 | 41 | 0.8 |

In Example 10, a preparation was obtained in which the disintegration time was similar to that of Comparative Example 13, but the tablet hardness was higher than that of Comparative Example 13.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A low-substituted hydroxypropylcellulose powder having:
a molar substitution number per anhydrous glucose unit of 0.05 to 1.0; an average particle size of 10 to 100 μm; a specific surface area measured by the BET method of at least 1.0 m$^2$/g; an elastic recovery ratio of not greater than 7% when compressed at a compression pressure of 50 MPa; and a repose angle of not greater than 42°,
wherein the elastic recovery ratio of the powder is calculated according to the following equation:

$$\text{Elastic recovery ratio} = \frac{(\text{tablet thickness after 30 seconds} - \text{minimum tablet thickness})}{(\text{minimum tablet thickness})} \times 100$$

wherein tablet thickness is determined for a tablet obtained by compression of the powder into a tablet with a weight of 480 mg and a compression force of 50 MPa using a flat shape with a flat contact face for a tablet diameter of 11.3 mm, wherein minimum tablet thickness is determined at its lowest point when the powder is compressed by an upper punch of a flat shape unit with a fixed lower punch, and tablet thickness after 30 seconds is the tablet thickness determined 30 seconds after the upper punch is removed.

2. The low-substituted hydroxypropylcellulose powder according to claim 1, having a swollen volume increase ratio of at least 300%, and a swollen volume increase rate of at least 100%/min, when absorbing water.

3. A solid dosage form comprising the low-substituted hydroxypropylcellulose powder according to claim 1.

* * * * *